(12) United States Patent
Yakovlev et al.

(10) Patent No.: US 10,466,166 B2
(45) Date of Patent: Nov. 5, 2019

(54) ELLIPSOMETRY SYSTEM FOR MEASURING MOLECULAR BINDING, ADSORPTION AND DESORPTION

(71) Applicant: Agency for Science, Technology and Research, Singapore (SG)

(72) Inventors: Nikolai Yakovlev, Singapore (SG); Laura Sutarlie, Singapore (SG); Dave Siak-wei Ow, Singapore (SG); Tandiono Tandiono, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/311,063

(22) PCT Filed: May 28, 2015

(86) PCT No.: PCT/SG2015/050130
§ 371 (c)(1),
(2) Date: Nov. 14, 2016

(87) PCT Pub. No.: WO2015/183201
PCT Pub. Date: Dec. 3, 2015

(65) Prior Publication Data
US 2017/0074781 A1    Mar. 16, 2017

(30) Foreign Application Priority Data
May 28, 2014    (SG) ............................ 10201402701Y

(51) Int. Cl.
*G01N 21/21* (2006.01)
*G01N 21/05* (2006.01)

(52) U.S. Cl.
CPC ........... *G01N 21/211* (2013.01); *G01N 21/05* (2013.01)

(58) Field of Classification Search
CPC ................. G01N 21/05; G01N 21/211; G01N 2021/052–058; G01N 2021/213–215
See application file for complete search history.

(56) References Cited

U.S. PATENT DOCUMENTS

| | | | | |
|---|---|---|---|---|
| 2,192,251 A | * | 3/1940 | Whittaker | G03B 27/16 74/1 R |
| 3,302,541 A | * | 2/1967 | Land | G03B 7/02 356/229 |
| 3,985,447 A | * | 10/1976 | Aspnes | G01N 21/211 356/369 |

FOREIGN PATENT DOCUMENTS

WO    WO-2011/113007 A2    9/2011

OTHER PUBLICATIONS

Written Opinion for PCT/SG2015/050130, 7 pages (dated Aug. 24, 2015).
(Continued)

*Primary Examiner* — Shawn Decenzo
*Assistant Examiner* — Rufus L Phillips
(74) *Attorney, Agent, or Firm* — Choate, Hall & Stewart LLP

(57) ABSTRACT

According to one aspect of the invention, there is provided an ellipsometry system for measuring any one or more of molecular binding, adsorption and desorption on a substrate, the system comprising: a) a cuvette comprising i) a body within which a cavity is formed and an opening on the body, wherein the cavity extends into the opening through which the substrate is immersed; ii) a window formed on each of two oppositely located walls of the body, wherein the windows are aligned to allow light to enter through one of the two windows to reflect off the portion of the substrate immersed in the cavity and exit through the other of the two windows; iii) a channel arrangement enclosed within the body of the cuvette and comprising two non-contiguous (Continued)

portions, wherein one of the two non-contiguous portions guides fluid into the cavity and the other non-contiguous portion guides fluid out of the cavity; b) a polarized light source disposed to provide the light that enters into one of the two windows on the body of the cuvette; and c) a detection stage disposed to receive the light that exits through the other of the two windows on the body of the cuvette, wherein the detection stage is configured to measure polarization rotation of the received light, the polarization rotation caused by any one or more of molecular binding, adsorption and desorption occurring on the substrate surface. The detection stage preferably contains a polarization modulator, which is configured to measure polarization rotation of the received light.

11 Claims, 12 Drawing Sheets

(56) References Cited

OTHER PUBLICATIONS

International Search Report for PCT/SG2015/050130, 7 pages (dated Aug. 24, 2015).

\* cited by examiner

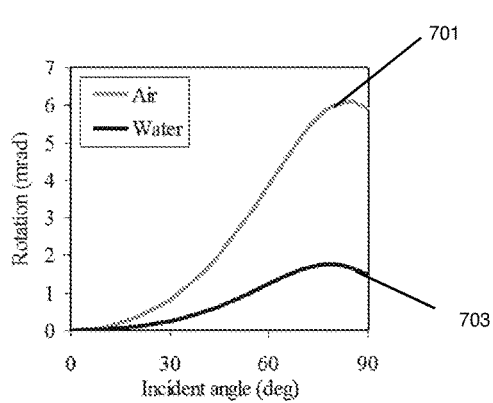
Figure 7B
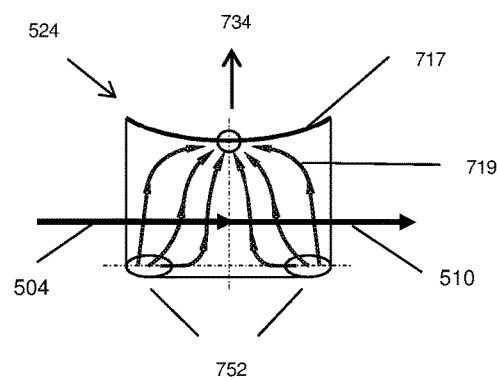
Figure 7C
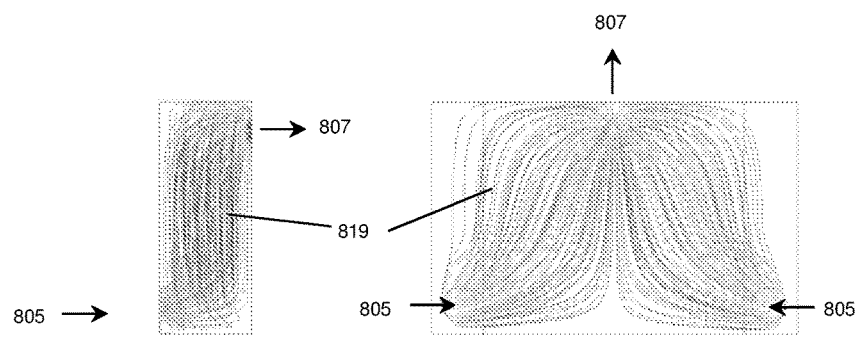
Figure 8A
Figure 8B

ELLIPSOMETRY SYSTEM FOR MEASURING MOLECULAR BINDING, ADSORPTION AND DESORPTION

CROSS REFERENCE TO RELATED APPLICATIONS

This patent application is a National Stage Entry of International Patent Application No. PCT/SG2015/050130, filed on May 28, 2015, which claims the benefit of priority of Singapore patent application No. 10201402701Y, filed on May 28, 2014, the contents of each of which are hereby incorporated by reference in their entirety for all purposes herein.

TECHNICAL FIELD

The present invention relates to an ellipsometry system for measuring any one or more of molecular binding, adsorption and desorption.

BACKGROUND ART

Ellipsometry is a technique which measures the change in polarization of light when reflected off a sample surface. It derives its sensitivity from the determination of the relative phase shift Δ between normal (p) and in-plane (s) components of polarization vector in the reflected light. The phase shift can be measured with precision of 0.1 degree, which translates to around 1 nm of organic material on silicon substrate in air.

Precision ellipsometry (PREL) is based on modulation of polarization, which further increases sensitivity to 0.01 mrad, which translates to 0.01 nm. This high sensitivity allows real time measurement of atomic and molecular attachment and detachment.

FIG. 1 shows a prior art system that is used for precision ellipsometry. Not shown are a light source, which produces linearly polarized light that is made incident 104 on a substrate 106 providing the sample surface, and a polarization analyser and detector 108 placed on the path of the reflected beam 110.

A cuvette 120 can be used to introduce a layer, where any one or more of molecular binding, adsorption and desorption occurs, onto the substrate 106 surface. The cuvette 120 is of closed flow type and has an inlet 122 and an outlet 124 only for liquid. The substrate 106 must be placed within the cuvette 120 in advance before closing and optical alignment. While the closed flow cuvette 120 allows quick exchange of solvent and solution, it requires a long time to change the substrate 106, because this involves draining of liquid before opening, draining of air after closing and alignment of the optical analysis system (not shown) for each substrate 106.

FIG. 2 shows a prior art immersion cuvette 220. The immersion cuvette 220 of FIG. 2 has an inlet 222 and an outlet 224 for liquid and an opening 226 through which a substrate 206 can be immersed. The advantage of this cuvette 220 is the possibility of fast changing the substrate 206 together with keeping all other parts of the system stable. Thus when a next substrate (not shown) is immersed, the system is ready for the next measurement. However liquid flow pattern is complicated because the inlet 222 and the outlet 224 are introduced from the top of the cuvette 220. Hence a magnetic stirrer 227 is required to achieve uniformity of the solution, and hence it is suitable to measure only slow kinetics, e.g. in the range of minutes.

Another optical technique for measurement of molecular binding is surface plasmon resonance (SPR), which is shown in FIG. 3. SPR relies on a measurement of refractive index change at a metal surface, when molecules attach to the surface. It works as follows: light 304 enters through a transparent substrate 306 at incidence angle $\theta_{SPR}$. The light 304 induces plasmon resonance in a gold (Au) layer 315; deposition of the layer 313 changes the value of the resonance angle. If incidence angle $\theta_{SPR}$ is fixed, it changes reflected intensity. Because surface plasmon wave is evanescent in the direction normal to the surface and propagates along the surface, it is very sensitive to the molecules near the surface and less sensitive to molecules far from the surface, or changes in the medium. However, SPR only works with noble metals (mostly gold), which limits the range of applications of this measurement technique.

There is thus a need to address the shortfalls of the measurement techniques described above.

SUMMARY OF INVENTION

According to one aspect of the invention, there is provided an ellipsometry system for measuring any one or more of molecular binding, adsorption and desorption on a substrate, the system comprising: a) a cuvette comprising i) a body within which a cavity is formed and an opening on the body, wherein the cavity extends into the opening through which the substrate is immersed; ii) a window formed on each of two oppositely located walls of the body, wherein the windows are aligned to allow light to enter through one of the two windows to reflect off the portion of the substrate immersed in the cavity and exit through the other of the two windows; iii) a channel arrangement enclosed within the body of the cuvette and comprising two non-contiguous portions, wherein one of the two non-contiguous portions guides fluid into the cavity and the other non-contiguous portion guides fluid out of the cavity; b) a polarized light source disposed to provide the light that enters into one of the two windows on the body of the cuvette; and c) a detection stage disposed to receive the light that exits through the other of the two windows on the body of the cuvette, wherein the detection stage is configured to measure polarization rotation of the received light, the polarization rotation caused by any one or more of molecular binding, adsorption and desorption occurring on the substrate surface. The detection stage preferably contains a polarisation modulator, which is configured to measure polarization rotation of the received light.

BRIEF DESCRIPTION OF DRAWINGS

Example embodiments of the invention will be better understood and readily apparent to one of ordinary skill in the art from the following written description, by way of example only, and in conjunction with the drawings. The drawings are not necessarily to scale, emphasis instead generally being placed upon illustrating the principles of the invention, in which:

FIG. 7B shows measurement of polarization rotation that results from 1 nm of organic layer on a silicon substrate in air and in water.

FIG. 7C shows a diagram of fluid flow lines within the cuvette shown in FIGS. 5A to 5C.

FIG. 8A shows a side view of fluid flow in the cuvette shown in FIGS. 5A to 5C.

FIG. 8B shows a front view of fluid flow in the cuvette shown in FIGS. 5A to 5C.

DETAILED DESCRIPTION

Figure 1:
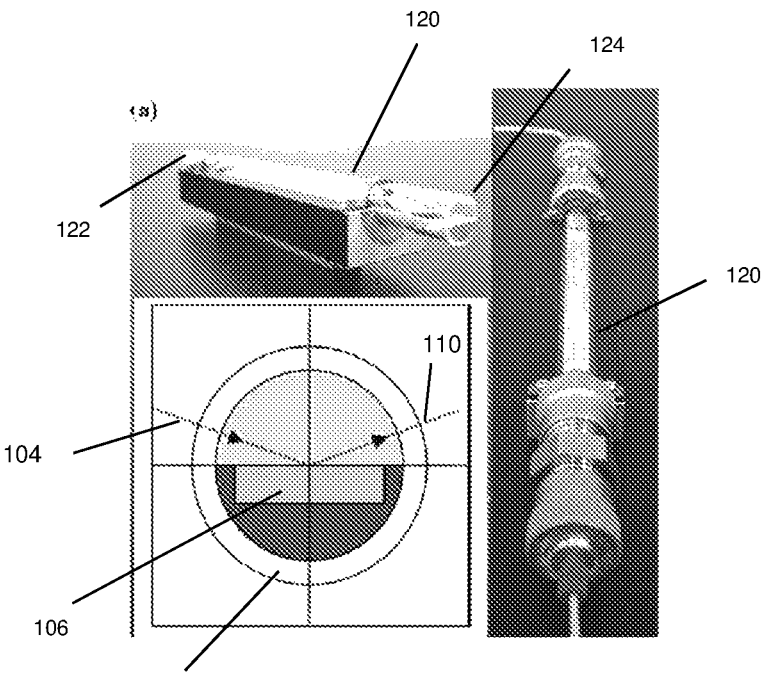
FIG. 1 shows a prior art closed flow through cuvette.

In the following description, various embodiments are described with reference to the drawings, where like reference characters generally refer to the same parts throughout the different views.

Figure 4A:
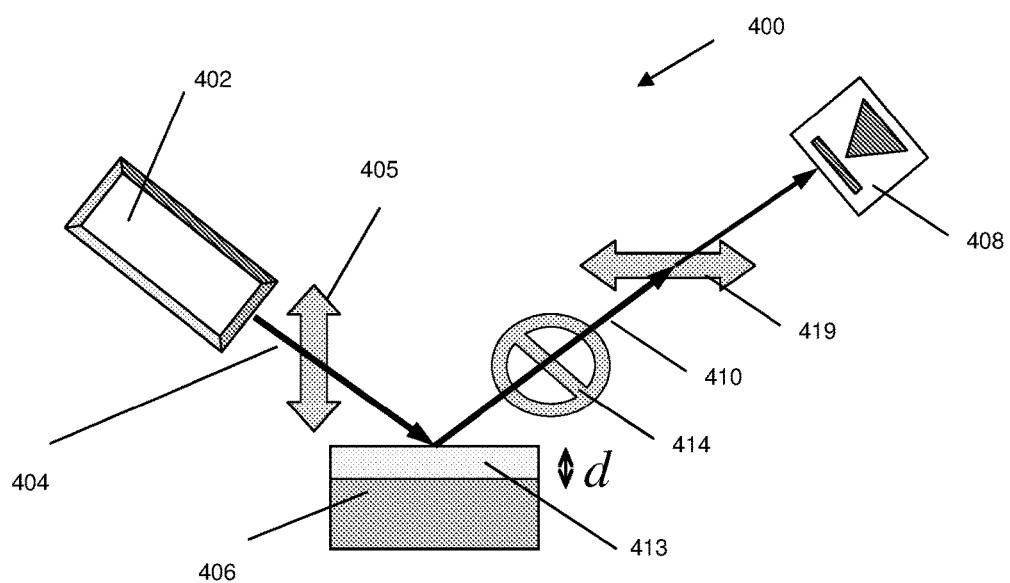
FIG. 4A shows a schematic of a system, in accordance with one embodiment of the present invention, for precision ellipsometry to measure any one or more of molecular binding, adsorption and desorption.

FIG. 4A shows a schematic of a system 400, in accordance with one embodiment of the present invention, for precision ellipsometry to measure any one or more of molecular binding, adsorption and desorption. The system 400 comprises a light source 402, such as a laser, having a polarizer 405 that produces linearly polarized light which is made incident 404 on a sample 406. A polarization analyser and detector 408 are placed on the path of the reflected beam 110.

Figures 4B, 4C, 4D:
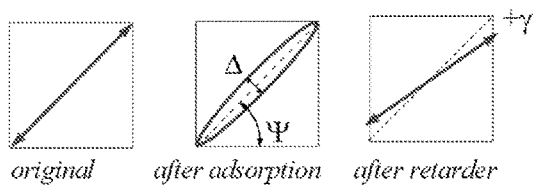
FIG. 4B shows measurement of a polarization signal received before molecular adsorption takes place in the system of FIG. 4A.
FIG. 4C shows measurement of a polarization signal received after molecular adsorption has occurred in the system of FIG. 4A.
FIG. 4D shows a polarization signal received after retardation in the system of FIG. 4A.

At an arbitrary incident angle when the sample 406 does not have a layer 413, both the incident ray 404 and the reflected ray 410 are linearly polarized, as shown in FIG. 4B. Deposition of the layer 413 changes polarisation of the reflected light 410 from linear to elliptic, as shown in FIG. 4C, where the phase shift Δ is proportional to the thickness d of the layer 413, as set out in equation (1) below, where the thickness d is less than wavelength of the polarised light. The polarisation analyser and detector 408 measures the ellipticity Δ in accordance with equation (2) below which is based on a photo-elastic modulator (PEM) or a Faraday rotation cell.

[Math. 1]

$$\Delta = 2\beta \frac{r_1^p r_2^s - r_2^p r_1^s}{\tan\Psi(r_1^s + r_2^s)^2} \quad (1)$$

[Math. 2]

$$\beta = \frac{2\pi d}{\lambda}\sqrt{n_1^2 - n_0^2 \sin^2\theta_1^i} \quad (2)$$

Figure 5A:
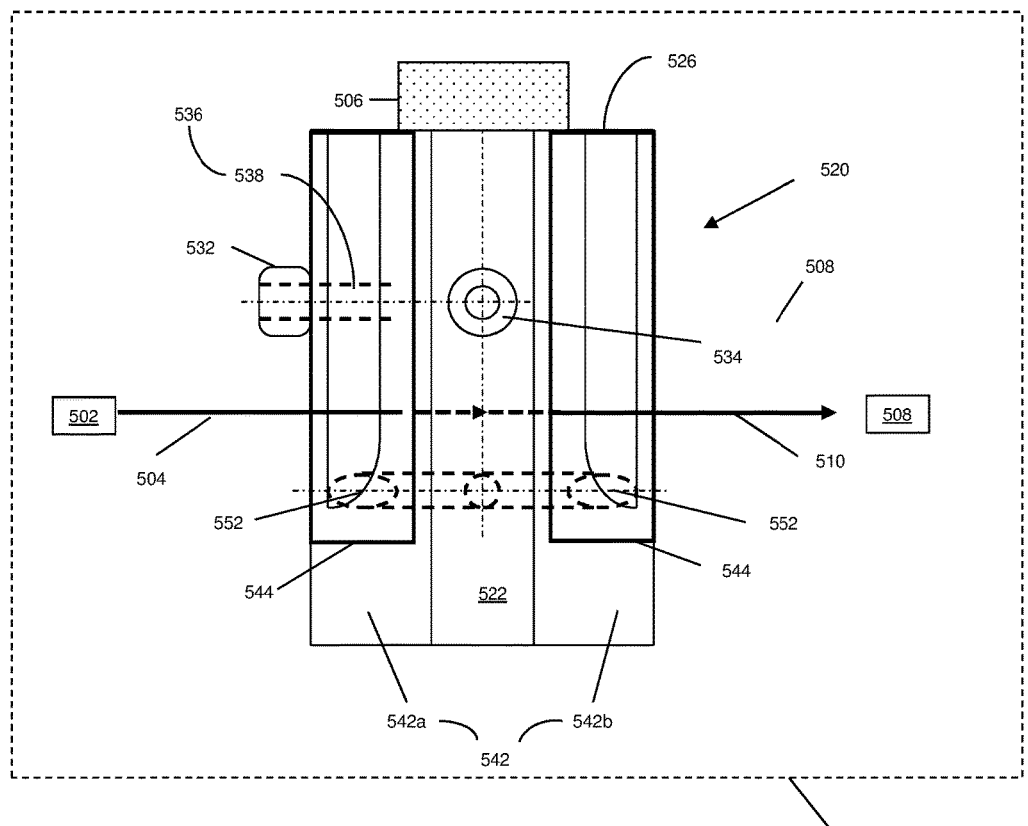
FIG. 5A shows a front view of a cuvette made in accordance with one embodiment of the present invention.
Figure 5B:
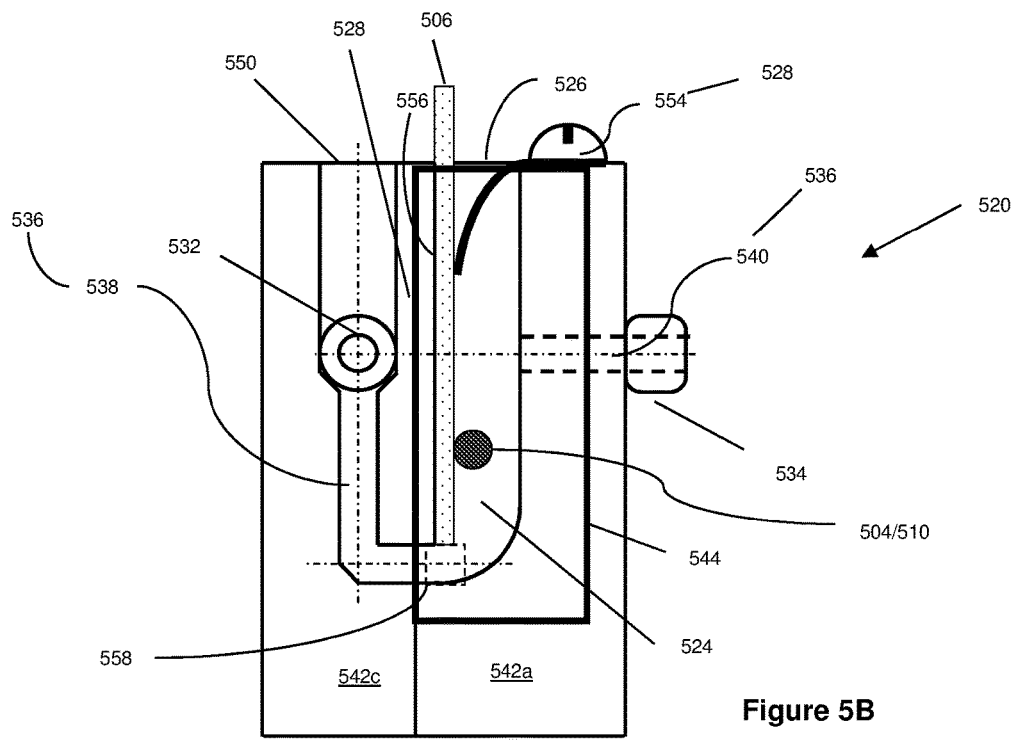
FIG. 5B shows a side view of the cuvette of FIG. 5A.

To measure the ellipticity of the reflected light, a quarter-wave retarder 414 is placed before the polarisation analyser 419 and detector 408. The retarder 414 converts ellipticity Δ into rotation γ, as shown in FIG. 4D, which is measured using the polarisation analyser 419 and detector 408. The rotation γ is proportional to the thickness d in accordance with equation (3) below.

$$\gamma = \Delta \sin\Psi \cos\Psi \quad (3)$$

where Ψ is angle of long axis of ellipse and Δ is phase shift between normal (p) and in-plane (s) components of reflected polarization vector shown in FIG. 1C FIGS. 5A to 5C show a front view, a side view and a top view respectively of a cuvette 520 made in accordance with one embodiment of the present invention. FIG. 5B is a side view of a partial cross-section of the cuvette 520, with a portion cut away to show the internal components of the cuvette 520. The features of the cuvette 520 are described with reference to FIGS. 5A to 5C.

With reference to FIG. 5A, the cuvette 520 comprises a body 522 within which a cavity 524 (see FIG. 5B) is formed and an opening 526 on the body 522. The cavity 524 is an empty space contained within the depth of the body 522 (i.e. the cavity 524 is not a through hole) and is for storing fluid.

The cavity 524 extends into the opening 526, so that the cavity 524 is accessible via the opening 526.

Figure 5C:
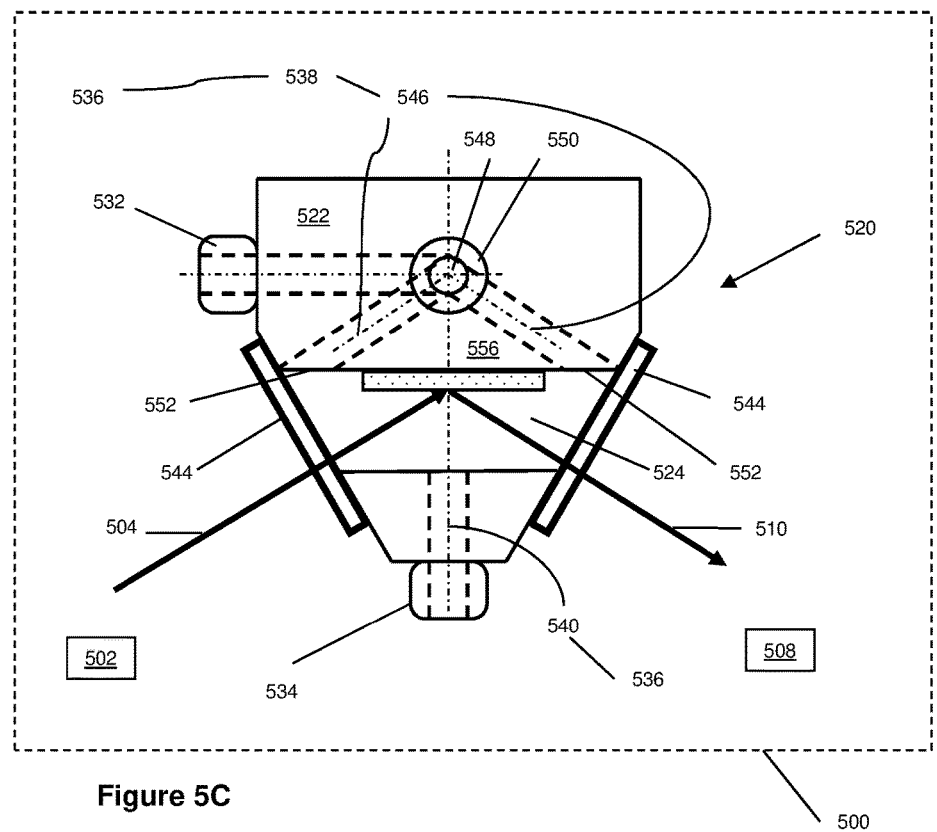
FIG. 5C shows a top view of the cuvette of FIG. 5A.

The body 522 comprises a support structure 528. The support structure 528 is adapted to hold the substrate 506 with at least a portion immersed in the cavity 524, i.e. the support structure 528 immerses at least a portion of a substrate 506 within the cavity 524. The support structure 528 thus provides the body 522 with a dedicated part that is designated to hold the substrate 506. During use, as shown in FIGS. 5A to 5C, the substrate 506 is inserted through the opening 526 to be placed on the receiving surface 556 of the support structure 528 within the cavity 524. In the embodiment shown in FIGS. 5A to 5C, at least the portion of the support structure 528 against which the substrate 506 lies is integral with the body 522 of the cuvette 520, i.e. that portion is unitary with the body 522. In another embodiment (not shown), the entire support structure 528 is manufactured separately from the body 522 and then affixed to the body 522.

Figure 2:
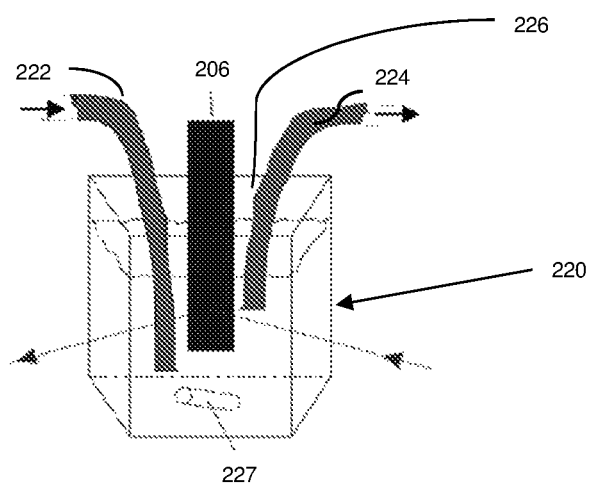
FIG. 2 shows a prior art immersion cuvette.

A fluid inlet 532 and a fluid outlet 534 are formed on the body 522. A channel arrangement 536 is enclosed within the body 522 of the cuvette 520. The channel arrangement 536 comprises two non-contiguous portions, with each non-contiguous portion extending into the cavity 524. One of the two non-contiguous portions guides fluid into the cavity 524 and the other non-contiguous portion guides fluid out of the cavity 524. The fluid inlet 532 and the fluid outlet 534 are each in fluid communication with the channel arrangement 536. The enclosed channel arrangement 536 provides an input conduit 538 between the fluid inlet 532 and the cavity 524, and an output conduit 540 between the cavity 524 and the fluid outlet 534. The input conduit 538 provides one of the two non-contiguous portions of the channel arrangement 536, while the output conduit 540 provides the other of the two non-contiguous portions of the channel arrangement 536. Since the cavity 524 is where the substrate 506 is located, the end of the input conduit 538 which is connected to the cavity 524 becomes the region where fluid that enters the fluid inlet 532 is first introduced to the substrate 506, while the end of the output conduit 540 which is connected to the cavity 524 becomes the region where this fluid is extracted from the cavity 524. Thus the enclosed channel arrangement 536 provides a means to control the fluid flow line pattern experienced by the substrate 506. Compared to simply providing the inlet 222 and the outlet 224 through the opening 226 of the cuvette 220 shown in FIG. 2, the enclosed channel arrangement 536 thus improves control over the fluid flow line pattern experienced by a substrate. The embodiment shown in FIGS. 5A to 5C has the channel arrangement 536 implemented as two separate conduits 538 and 540, with each provided in a different wall or part of the body 522. However, it will be appreciated that other configurations (not shown) may have the channel arrangement 536 disposed within a same part or wall of the body 522. Further, the part of the body 522 where the channel arrangement 536 is located can be varied, so that desired flow lines can be achieved.

The body 522 has several walls 542 with each wall providing a planar surface. A window 544 is formed on each of two oppositely located walls 542a and 542b of the body 522. These walls 542a and 542b are oppositely located in that the walls 542 and 542b are located on other sides of the body 522. The windows 544 are aligned to allow light to enter 504 through one of the two windows 544 to reflect off the portion of the substrate 506 suspended within the cavity 524 and exit 510 through the other of the two windows 544. Thus, the provision of the support structure 528 ensures that any substrate 506 is placed in a position to reflect the light from one of the two windows 544 to the other of the two windows 544. Such an alignment reduces the need to perform optical realignment when the substrate 506 is changed, since the support structure 528 ensures that the substrate 506 will be placed in the same position. Achievement of this alignment may thus be considered during determination of the location of the support structure 528 within the body 522 of the cuvette 520.

The cuvette 520 is a component of an ellipsometry system 500 that is shown in FIGS. 5A and 5C. The ellipsometry system 500 includes a polarized light source 502 and a detection stage 508. The polarized light source 502 is disposed to provide the light 504 that enters into one of the two windows 544 on the body 522 of the cuvette 520. The detection stage 508 is disposed to receive the light 510 that exits through the other of the two windows 544 on the body 522 of the cuvette 520. The detection stage 508 is configured to measure polarization rotation of the received light 510, wherein the polarization rotation is caused by any one or more of molecular binding, adsorption and desorption occurring on the substrate 506 surface.

The channel arrangement 536 comprises the input conduit 538 that is coupled at one end to the fluid inlet 532 and coupled to the cavity 524 at the other end. As shown in FIG. 5B, the input conduit 538 extends into the cavity 524 by going around a segment 558 of the portion of the support structure 528 suspended within the cavity 524. This segment 558 of the support structure 528 is, in one embodiment, located at the bottom of the support structure 528, the bottom being located within the cavity 524.

In the embodiment shown in FIGS. 5A to 5C, the input conduit 538 comprises two branches 546, wherein each of the two branches 546 has one end that meets at a common region 548 for coupling to the fluid inlet 532 and the other end is coupled to opposite regions 552 of the cavity 524 relative to the portion of the support structure 528 suspended within the cavity 524. In one embodiment, these opposite regions 552 are located at opposite corners of the cavity 524, whereby such a location ensures that fluid flow does not have stagnant corners. In an alternative configuration (not shown), the input conduit 538 comprises of only a single branch which directly connects the fluid inlet to the cavity.

The channel arrangement 536 also comprises the output conduit 540 that is coupled at one end to the fluid outlet 534 and coupled to the cavity 524 at the other end. Unlike the input conduit 538 of the embodiment shown in FIGS. 5A to 5C, the output conduit 540 is a singular branch.

The support structure 528 has a surface 556 that receives the substrate 506 and an opposite surface that faces the input conduit 538 of the channel arrangement 536. This receiving surface 556 of the support structure 528 is the surface against which the substrate 506 rests. In addition, the support structure 528 has a biasing element 554 that urges the substrate 506 against the receiving surface 556.

Although the biasing element 554 used in the embodiment shown in FIGS. 5A to 5C is a leaf affixed on one end to the body 522 of the cuvette 520, with the other end used to apply pressure on the substrate 506, the biasing element 554 may also any one or more of a screw and a clip, although these alternative configurations are not shown.

The body 522 of the cuvette 520 further comprises a reagent inlet 550 that extends into the channel arrangement 536 which is in fluid communication with the fluid inlet 532. In the embodiment shown in FIGS. 5A to 5C, the reagent inlet 550 thus extends into the input conduit 538. The reagent inlet 550 provides a port into which reagent is introduced into the cavity 524, whereby the reagent is transported to the cavity 524 via fluid introduced into the cuvette 520 through the fluid inlet 532. The reagent inlet 550 is on the same surface of the body 522 where the opening 526, into which the cavity 524 extends, is located. The opening 526, the fluid inlet 532 and the fluid outlet 534 are located on different surfaces of the body 522 of the cuvette 520.

Figure 6:
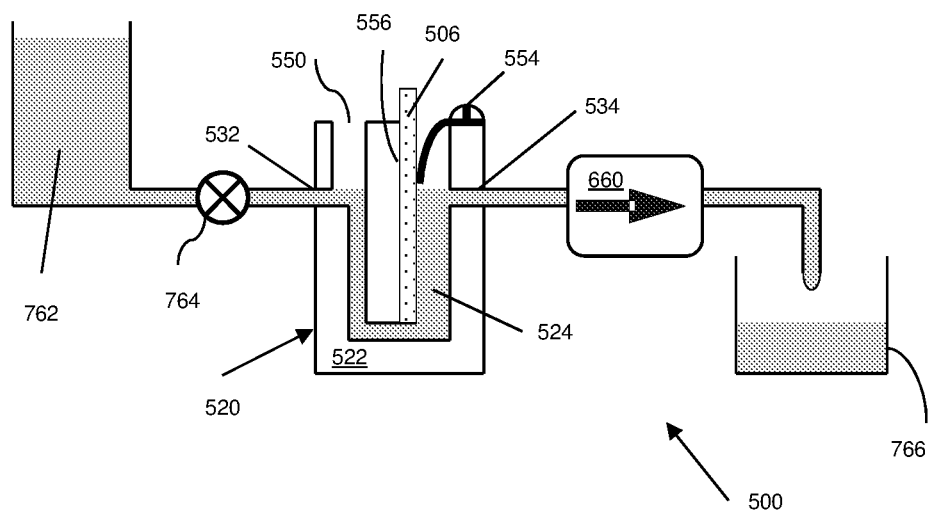
FIG. 6 shows the ellipsometry system, in accordance with one embodiment of the invention, comprising a pump.

The ellipsometry system 500 may further comprise a pump 660 coupled to the fluid outlet 534 of the body 522 of the cuvette 520, as shown in FIG. 6. The pump 660 may be a peristaltic pump, which can pump either air or liquid. The pumping rate may be set higher than the inlet flow rate, hence the constant pumping keeps the liquid level constant with or without liquid inlet flow into the fluid inlet 532. If reagent or solvent is injected into the cuvette 520 faster than the pumping rate, they will overflow. To prevent this, the volume above the outlet 534 is a reserve for in case reagents are too injected too quickly. Further fluidic accessories that the ellipsometry system 500 may have are a solvent source vessel 762 which is coupled to the body 522 via the fluid inlet 532 of the cuvette 520 via a flow control valve 764. The pump 660 may also be coupled to a drain vessel 766.

Returning to FIGS. 5A to 5C, the cuvette 520 holds the substrate 506 in order to measure molecular adsorption of reagent that is transported to the substrate 506 by the fluid that that is injected into the fluid inlet 532 The cavity 524 of the cuvette 520 provides a reservoir that can contain a sufficient quantity of fluid to submerge the portion of the substrate 506 where any one or more of molecular binding, adsorption and desorption is being observed.

Figure 7A:
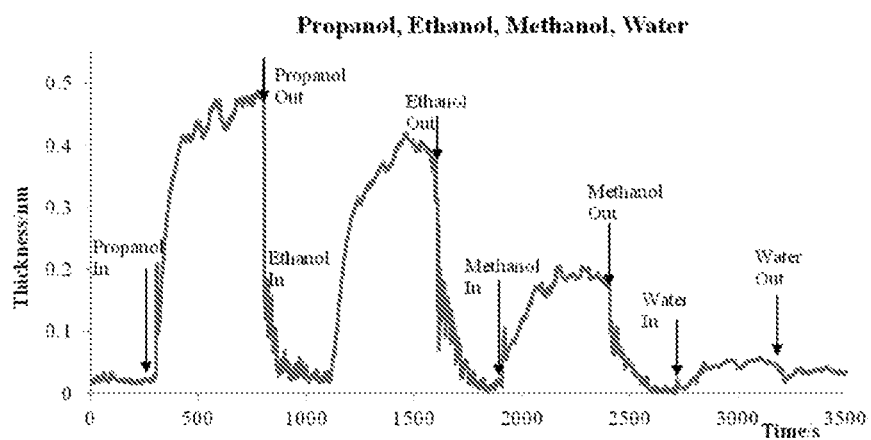
FIG. 7A shows a graph which plots the thickness of adsorption when using each of various solvents.

Each of the two windows 544 is orientated to allow polarised light to transmit through perpendicularly; so that any molecules deposited on the windows 544 do not affect light polarization. In order to examine any possible interference of glass on measurement of molecular adsorption (i.e. in considering the impact of using glass to fabricate each of the two windows 544), a gas chamber with glass windows was made (not shown) and experiments using the vapour of propanol, ethanol, methanol and water confirmed that adsorption of molecules on the substrate could be reproducibly measured. FIG. 7A shows a graph which plots the thickness of adsorption when using each of these vapours. The requirement of glass windows to be perpendicular to the light applies for molecular layers in liquid, because the value of polarization rotation will be smaller than those of vapour. FIG. 7B shows polarization rotation that results from 1 nm of organic layer on a silicon substrate in air (curve 701) and in water (curve 703).

The cuvette 520 is able to secure the substrate through the support structure 528 and allows substrate exchange as well as light beam adjustment. The fluid inlet 532 and the fluid outlet 534 allow fluid, such as solvent, to pass in and out of the cuvette 520. The reagent inlet 550 allows quick injection of reagent, such as solutions of molecules intended for interaction with the substrate 506, where the fluid outlet 534 allows the reagent to be removed via the fluid introduced through the fluid inlet 532.

The body 522 of the cuvette 520 may be made of, for example, acrylic slab, plastic, metal, glass or ceramic. The substrate 506 may be of made from any material, such as plastic, insulator or semiconductor, with a reflecting surface. The fluid that is introduced through the fluid inlet 532 may be aqueous solution, inorganic salt solution or solutions in organic solvents. Reagent that is introduced into the reagent inlet 550 may include any one or more of organic molecules, polymers and biomolecules. The biomolecules may include any one or more of protein, nucleic acids, sugar, peptides, enzyme, cell and cell membrane.

The cavity 524 provides for a fluidic reservoir in front of the substrate 506. In the embodiment shown in FIGS. 5A to 5C, the cavity 524 has the shape of a vertical trapezoidal prism having slanted sides defined by the opposing walls 542$a$ and 542$b$. In another embodiment (not shown), the cavity may have a triangular shape. Each of the opposing walls 542$a$ and 542$b$ has an optical window 544 made of inorganic transparent material, for example, glass or quartz. In order to provide incoming light 504 at an angle $\theta$ to the substrate 506 normal, the window 544 is preferably slanted at the same angle $\theta$ with respect to the substrate 506, so that the incoming light 504 is perpendicular to the plane of the window 544 of the wall 542$a$. Similarly, the reflected light 510 is also perpendicular to the plane of the window 544 of the wall 542$b$. The substrate 506 is held using the biasing element 554 against the rigid back wall of the cavity 524, the rigid back wall being provided by the support structure 528. This allows any substrate to be immersed from the top of the cuvette 520 and stand rigidly at the same position, which keeps light beam adjustment.

The input conduit 538 that is located between the support structure 528 and a rear wall 542$c$ (see FIG. 5B) of the body 522 of the cuvette 520 provides a fluidic channel that allows introduction of fluid (via the fluid inlet 532), such as liquid, and reagent (via the reagent inlet 550), such as solution, into the opposite regions 552 located at the base of the cavity 524. In the embodiment shown in FIGS. 5A to 5C, these opposite regions 552 are located at the bottom corners of the cavity 524. In an alternative configuration (not shown), the fluidic channel provided by the input conduit does not connect to the base of the cavity, but may connect to the cavity at, for example, between the base of the cavity and the height at which the fluid outlet 534 is located. The fluid outlet 534 is located around the middle height of the body 522, away from the path of the incoming and outgoing light 504 and 510. With reference to FIG. 7C, the design of the cuvette 520 allows fluid flow lines 719, within the cavity 524, that start from the inlets 752 of the cavity 524 (corresponding to the opposite regions 552 shown in FIGS. 5A and 5C) and end at the outlet 734 of the cavity 524, the outlet 734 leading to the fluid outlet 534 shown in FIGS. 5A to 5C. It will be appreciated that there are no standing corners; the bottom corners (i.e. the opposite regions 552) are inlets to the cavity 524, while the top corner is formed by meniscus 717 of the fluid in the cavity 524, i.e. a free surface.

FIGS. 8A and 8B respectively show a side view 801 and front view 803 of fluid flow in the cuvette 520, shown in FIGS. 5A to 5C, as studied using computational fluid dynamics simulation. The two inlets 752 (shown in FIG. 7C) located at the bottom of the cavity 524 are represented using reference numeral 805, while reference numeral 807 represents the outlet 734 located at the top of the cavity 524. The flow pattern is shown by the particle path lines 819. The liquid sample injected into the cuvette 520 via the two inlets 805 flow upward leaving the cuvette 520 via the outlet 807. Most of the liquid passes through the centre of the cuvette 520 where the substrate 506 is attached and the dead corner is relatively insignificant.

The cuvette 520 shown in FIGS. 5A to 5C has several applications which include real time study of chemical reactions, where one reagent is immobilised on a reflecting substrate and the other is supplied from the solution; heterogeneous catalysis; monitoring of production in chemical technology; imaging, if equipped with an array detector;

quantitative and qualitative analysis of binding of biological solutions and suspensions; and studying fouling and anti-fouling processes.

Figure 9A:
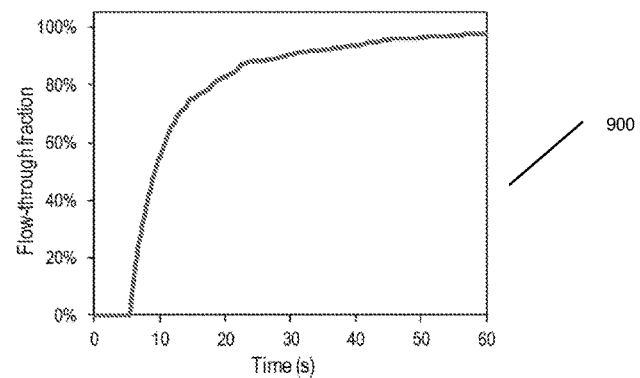
FIG. 9A shows a plot of flow-through fraction against time obtained from using the cuvette shown in FIGS. 5A to 5C.

FIG. 9A shows a plot 900 of flow-through fraction against time of the cuvette 520 shown in FIGS. 5A to 5C. The design of the cuvette 520 allows quick solution exchange. It only needs less than 10 seconds to replace half of the solution, which is mostly in the centre of the cuvette 520. More than 90% of the liquid is replaced with fresh liquid in less than 30 seconds. For the plot 900, the liquid is injected at 0.01 m/s. Shorter replacement duration is expected when a higher inlet velocity is used. These results also show that the quick removal of the solution in the cuvette is comparable to a "flow-through" cuvette.

The procedure for specific molecular binding measurements using the cuvette 520 shown in FIGS. 5A to 5C is carried out by immobilising a receptor molecule on the substrate 506 and applying a target molecule in a solution. This is so called heterogeneous or solid-liquid phase detection. The substrate 506, cleaned using wet chemistry, is immersed into the cuvette 520 filled with liquid injected into the cuvette 520 through its fluid inlet 532. This allows molecules inside the injected liquid to immobilise on the substrate 506 surface. The optical system, provided by the polarized light source 502 and the detection stage 508 is adjusted to get a first polarization signal reading. Then liquid is passed through the cuvette 520 to obtain a stable environment and optical signal recording is started. At a certain moment, the flow of liquid is stopped and a respective reagent (i.e. the receptor or the target) is injected into the reagent inlet 550, while excess of liquid is removed through the fluid outlet 534 by the pump 660 (see FIG. 6). A second polarization signal reading is then obtained. If the reagent binds to the surface of the substrate 506, then polarization rotation increases showing the increase of thickness of a layer formed by the reagent bound to the surface of the substrate 506. However, if there is a decrease of rotation, it means removal of molecules from the surface of the substrate 506. The difference between the polarization rotation of the first reading and the second reading is proportional to average thickness of a layer formed by the reagent on the substrate 506 surface.

If the solutions (i.e. both the liquid injected through the fluid inlet 532 and the reagent injected through the reagent inlet 550) used are transparent, measurement of the binding can be done in real time, because the rotation of polarization can be continuously recorded. The real-time measurement allows for kinetic analysis for specific surface binding process. The design of the cuvette, which enables fast change of solvent to solution and vice versa, allows measurements of kinetics as fast as in seconds.

If the solutions used are not transparent, the ellipsometry system 500 still enables quantitative measurement of the amount of molecules that bind to the surface of the substrate 506 by comparing signal at rinsing level before injection of the solution and after removal of the solution. The difference between these levels can be converted to the amount of attached material (although kinetics may be not visible). This method of measurement by comparing rinsing levels is useful for analysis of biological solutions and suspensions.

Figure 9B:
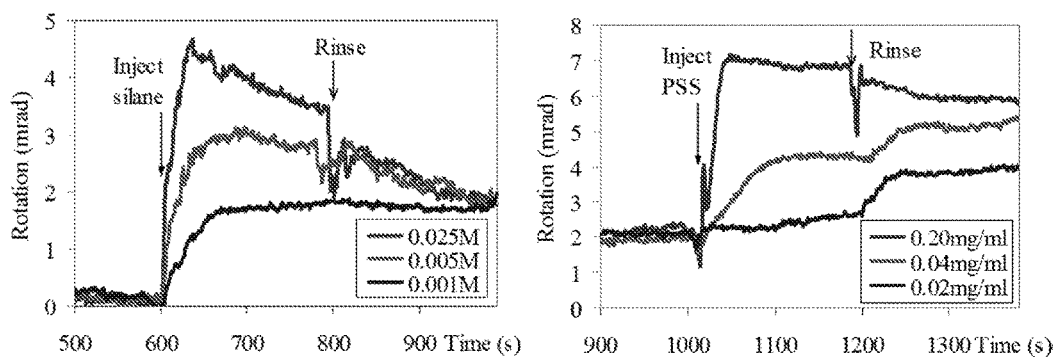
FIG. 9B shows the results obtained from real-time measurement of surface binding using the cuvette shown in FIGS. 5A to 5C.

FIG. 9B shows the results obtained from real-time measurement of surface binding using the cuvette 520 shown in FIGS. 5A to 5C. Firstly a solution of aminosilane is injected into the fluid inlet 532. The aminosilane binds to an oxidised Si sample used for the substrate 506 through formation of covalent bonds. At higher concentration, the binding is faster, while after rinsing, the final thickness is the same: around 1 nm, indicating irreversible attachment of one molecular layer. Subsequently solution of poly-styrene-sulfonate (PSS) is injected into the reagent inlet 550. The negatively charged PSS binds to the surface of the substrate 506 through electrostatic interaction with the positively charged amino-groups —NH3+. Here the concentration affects not only attachment rate, but also the final thickness, because polymers can attach to surfaces in different conformations. In this example, aminosilane is the receptor and PSS is the target. It is seen that attachments of both aminosilane and PSS are irreversible, i.e. the flow of water does not remove the molecules. It is seen also that kinetics of attachment depends differently on concentration, indicating different processes during attachment of small molecules and polymers.

The cuvette 520 shown in FIGS. 5A to 5C allows for real-time monitoring of the rate and progress of chemical reactions, as opposed to methods which extract samples of the reaction mixture at various period of time for analysis to determine the amount of product and precursors present at each point of time. Such methods are troublesome and complicated and are incapable of detecting the rate and progress as the reaction proceeds. Unlike other real-time monitoring systems which use expensive and complicated equipment like nuclear magnetic resonance and require technical expertise, the cuvette 520 provides a cost effective apparatus to facilitate real-time monitoring.

Figure 3:
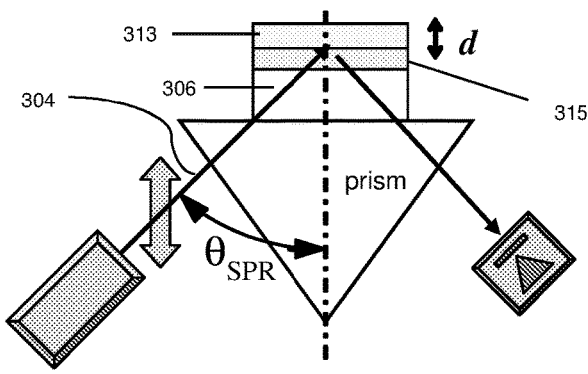
FIG. 3 shows prior art measurement of molecular binding using surface plasmon resonance.

There are existing ellipsometry systems that use the same underlying principle employed by the cuvette 520 shown in FIGS. 5A to 5C, i.e. molecular interaction where a precursors (or receptor) is immobilised on a substrate, while a target molecule is introduced in the surrounding medium, followed by measurement of the attachment, detachment, or reaction between the molecules. In monitoring changes in thickness of a layer on the substrate, standard ellipsometry has a precision of around 1 nm in gas and vacuum, and around 10 nm in liquid. To monitor molecular layers in the order of a nanometer, there are several techniques based on special substrates, such as surface plasmon resonance (SPR) described with reference to FIG. 3. SPR requires a gold layer 315 on the substrate 306. Quartz crystal microbalance (QCM) requires quartz crystal substrate with electrodes, while dual polarisation interferometry (DPI) requires two waveguides in the substrate. All these substrates are more expensive than those used for ellipsometry. Further, SPR only works with noble metal (mostly gold) surface; QCM uses metal (gold, silver, copper) and metal coated with a thin layer of metal oxide ($TiO_2$ or $SiO_2$). DPI is limited to silicon nitride.

The cuvette 520 shown in FIGS. 5A to 5C is advantageous over SPR because it works on the principle of ellipsometry and can use any substrate (such as plastic, insulator, or semiconductor) with a reflecting surface. The cuvette 520 shown in FIGS. 5A to 5C enables measurement of the kinetics of surface binding process with high precision and at low price. Cost reduction is possible by use of inexpensive reflecting substrates and a polarization modulator, such as the one described in greater detail with reference to FIGS. 10A to 10F. The polarization modulator described with reference to FIGS. 10A to 10F provides high precision of ellipsometry measurement (down to 0.1 nm of organic molecules in water).

Figure 10A:
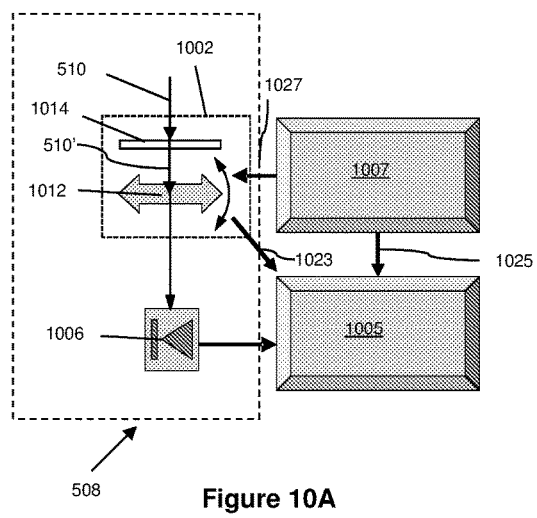
FIG. 10A shows a functional schematic of a detection stage in accordance with one embodiment of the present invention.

FIG. 10A shows a functional schematic of the detection stage 508 shown in FIGS. 5A and 5C. The detection stage 508 does not necessarily have to be used in tandem with the cuvette 520 of FIGS. 5A to 5C, since the detection stage 508 is configured to measure rotation which polarized light, generated from a source, may experience after modulation. Such polarization rotation may occur, for instance, when polarized light is reflected from molecular adsorption occurring on a substrate surface.

The detection stage 508 comprises a modulator stage 1002 and a detector 1006. The modulator stage 1002 and the detector 1006 are disposed along the path of the light 510 that is transmitted from the window 544 on the wall 542b of the cuvette 520 (see FIG. 5A). A function generator 1007 and a phase-lock amplifier 1005 are electrically coupled to the detection stage 508. The function generator 1007 is electrically coupled to the modulator stage 1002 and the phase-lock amplifier 1005 is electrically coupled to the detector 1006. The function generator 1007 is electrically coupled to the phase-lock amplifier 1005. Use of phase-lock detection of light intensity allows measurement of rotation of polarization of the light 510 with precision in the order of microradian.

The modulator stage 1002 comprises a retarder 1014 and a polarizer 1012. The retarder 1014 is disposed in the path of the received light 510 to convert the state of polarization of the received light 510 into a polarization suitable for the polarizer 1012. The polarizer 1012 is disposed to receive light 510' transmitted through the retarder 1014, the transmitted light 510' having been converted into a polarization state suitable for the polarizer 1012 by the retarder 1014. The polarizer 1012 may be a polaroid or a dichroic sheet. The modulator stage 1002 further comprises a drive mechanism coupled to the polarizer 1012. The drive mechanism is coupled to the polarizer 1012 to modulate the polarization of the light transmitted through the retarder 1014 (i.e. the light 510'). The drive mechanism is configured to move the polarizer within a plane generally perpendicular to the direction of the received light 510. The detector 1006 is disposed downstream of the polarizer 1014 to receive light transmitted through the polarizer 1014. Accordingly, the polarizer 1012 is located between the retarder 1014 and the detector 1006.

The movement that the drive mechanism causes the polarizer 1012 to undertake is over an angle range which is similar to the polarization rotation that the light 510' (i.e. light transmitted through the retarder 1014) has compared to the light 504 that enters the window 544 on the wall 542a of the cuvette 520 (refer FIG. 5A). Measurement of the movement that the drive mechanism makes would then be reflective of the polarization rotation that has occurred. The drive mechanism is elaborated below with reference to FIGS. 10B to 10F. In FIGS. 10B to 10F, the retarder 1014 is omitted for the sake of simplicity.

Figure 10B:
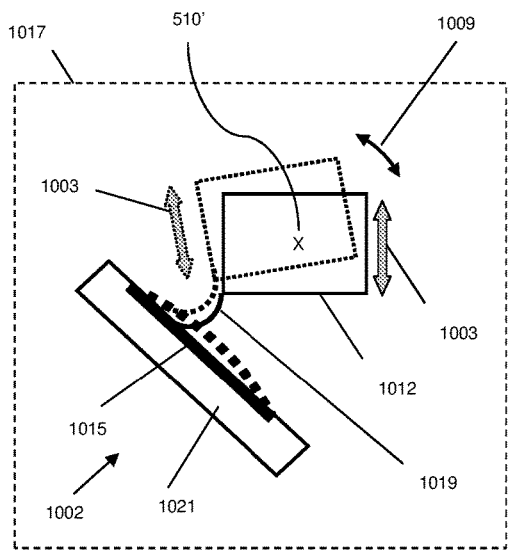
FIG. 10B shows a schematic of a first implementation of the drive mechanism shown in FIG. 10A.

FIG. 10B shows a schematic of a first implementation of the drive mechanism described with reference to FIG. 10A. The drive mechanism comprises an actuator 1015 coupled to the polarizer 1012, wherein the actuator 1015 is configured to move or slant the polarizer 1015 along an arc 1009 that lies in the plane 1017, the plane 1017 being generally perpendicular to the direction of the light 510' (denoted with the cross "x") transmitted through the retarder 1014. This plane 1017 is also generally perpendicular to the direction of the received light 510, since the transmitted light 510' results from the light 510 received by the retarder 1014 and is along the same path as the received light 510. The arrows 1003 show the direction of polarization of the polarizer 1012. While the embodiment shown in FIG. 10B has the actuator 1015 coupled to the polarizer 1012 through an elastic element 1019, such as a spring, another configuration (not shown) may have the actuator directly coupled to the polarizer. The actuator 1015 is coupled to a shelf 1021.

FIG. 10B uses bold lines to depict the actuator 1015, the polarizer 1012 and the spring 1019 at rest. Dashed lines are used to depict the actuator 1015, the polarizer 1012 and the spring 1019 when the actuator 1015 is activated, bringing about the arc movement 1009. When the actuator 1015 is realised using a piezo-electric actuator, the piezo-electric actuator is activated by applying an oscillating voltage. The piezoelectric actuator then bends and induces bending of the spring 1019, which may be an elastic element or an elastic strip, and tilts the polarizer 1012 to trace the arcuate path 1009. The tilt of the polarizer 1012 produces an oscillating tilt of polarization of the light 510 transmitting through the modulator stage 1002 (refer FIG. 10A). Maximum tilt is achieved, when frequency of the applied voltage coincides with resonant frequency determined by the mass of the polarizer 1012 and stiffness of the spring 1019. To decrease the operating voltage and/or size of the piezoelectric actuator, the frequency of the applied voltage may be set to coincide with the resonant frequency determined by the mass of the polarizer 1012 and stiffness of the spring 1019. In the embodiment shown in FIG. 10B, the actuator 1015 is a piezo-electric strip. In another embodiment (not shown), the actuator may be a bimetallic strip.

Figure 10C:
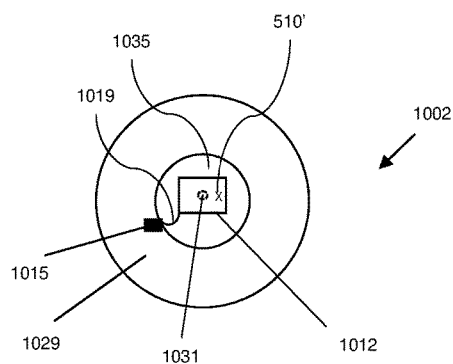
FIG. 10C shows a schematic of implementation of polarisation modulator with polarizer suspended on several springs.

FIG. 10C shows a front view a schematic of a second implementation of the drive mechanism described with reference to FIG. 10A. The drive mechanism comprises a platform 1029 coupled to the polarizer 1012, wherein the platform 1029 is arranged to rotate around an axis 1031 that is generally parallel to the path of the received light 510, so that the rotating platform 1029 is configured to rotate the polarizer 1021 on the plane that is generally perpendicular to the direction of the received light 510. The rotating platform 1029 may have the actuator 1015, which is coupled to the polarizer 1012 via the spring 1019. Similar to the embodiment shown in FIG. 10B, the actuator 1015 may be a piezo-electric strip or a bimetallic strip. The rotating platform 1029 has an opening 1035 over which the polarizer 1012 is suspended, the opening 1035 allowing the light 510' to pass through to the detector 1006 (see FIG. 10A).

Figures 10D, 10E:
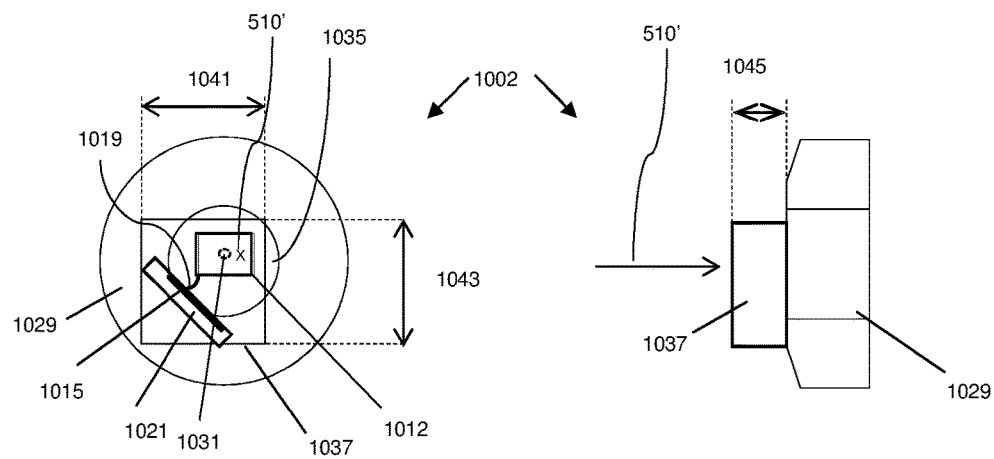
FIG. 10D shows a front view of a schematic of a second implementation of the drive mechanism shown in FIG. 10A.
FIG. 10E shows a front view of a schematic of a third implementation of the drive mechanism shown in FIG. 10A.

FIGS. 10D and 10E respectively show a front view and a side view of a schematic of a third implementation of the drive mechanism described with reference to FIG. 10A. The third implementation combines the platform 1029 of FIG. 10C with the drive mechanism shown in FIG. 10B. The drive mechanism of the third implementation comprises the platform 1029 coupled to the polarizer 1012, wherein the platform 1029 is arranged to rotate around an axis 1031 that is generally parallel to the path of the light 510' transmitted through the retarder 1014, so that the rotating platform 1029 is configured to rotate the polarizer 1012 on the plane that is generally perpendicular to the direction of the light 510'. The rotating platform 1029 has an opening 1035 over which the polarizer 1012 is suspended, the opening 1035 allowing the received light 510' to pass through to the detector 1006 (see FIG. 10A). The platform 1029 is coupled to the polarizer 1012 through the shelf 1021 mounted on the platform 1029, wherein the shelf 1021 has the actuator 1015 that is coupled to the polarizer 1012 through the spring 1019. As described with reference to FIG. 10B, the actuator 1015 allows the polarizer 1015 to move along an arc 1009 that lies in the plane generally perpendicular to the direction of the light 510'. The polarizer 1012, the shelf 1021, the spring 1019 and the actuator 1015 are housed within a protection box 1037 mounted on the platform 1029, wherein the shelf 1021 is coupled to the polarizer 1012 through the spring 1019

The rotating platform 1029 provides a rotation stage to which the actuator 1015 is attached. The rotating platform 1029 allows setting the mean direction of polarization. While polarization modulation is preferably performed by the arcuate motion brought about by the actuator 1015 coupled to the polarizer 1015, to analyse the polarization rotation of the received light 510, the polarization modulation can be alternatively undertaken by the rotation stage provided by the rotating platform 1029. In this alternative undertaking, the rotation stage sets the mean direction to extinction and the light that passes through the polarizer 1015 depends on the rotation of polarization of the incoming light 510.

Figure 10F:
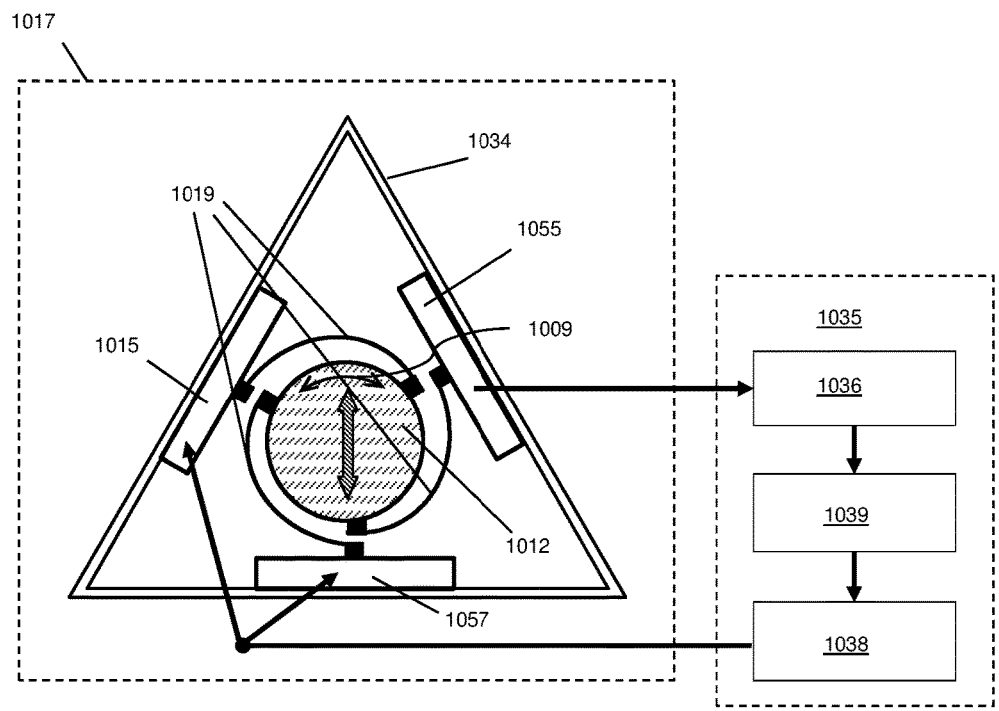
FIG. 10F shows a side view of a schematic of the third implementation of the drive mechanism shown in FIG. 10E.

In an alternative configuration shown in FIG. 10F, the polarizer 1012 is suspended using a plurality of spatially arranged elastic elements 1019. In the embodiment shown in FIG. 10F, the plurality of elastic elements 1019 are identical and spatially arranged to be each equally spaced apart. From mechanics based on Hooke's law, this serves to convert external vibration to translational movement of the polarizer 1012 along the plane 1017. In this alternative configuration, there is at least one further actuator 1055, 1057 with each coupled to one of the plurality of elastic elements 1019, wherein the plurality of actuators 1015, 1055 and 1057 are configured to move the polarizer 1012 along an arc 1009 that lies in the plane 1017. In the alternative configuration shown in FIG. 10F, any one of the plurality of actuators 1015, 1055 and 1057 may act as a sensor to measure the magnitude of the arc 1009, so that there is a sensor coupled to at least one of the plurality of elastic elements 1019. However, it will be appreciated that one or more additional elastic elements (not shown) may serve as the one or more sensors to measure the arc 1009 rotation.

In the embodiment shown in FIG. 10F, the actuator 1055 is arbitrarily chosen as the sensor. This is realised by connecting the actuator 1055 to an amplifier 1036 that receives an electrical signal generated when the actuator 1055 senses movement of the polarizer 1012 brought about by activation of the actuators 1015 and 1057 from being driven by a generator of driving voltage 1038, to which the actuators 1015 and 1057 are coupled. The actuators 1015 and 1055 and the actuator 1055, acting as a sensor, are fixed in a rigid box 1034. From the sensor (i.e. the actuator 1055), a signal goes to a self-tuning generator 1035 comprising the amplifier 1036, a phase shifting circuit 1039 and the generator of driving voltage 1038, which goes to drive the plurality of actuators 1015 and 1057 at resonance. The phase shifting circuit 1039 is tuned to achieve maximum amplitude of oscillations of the polarizer 1012 through the plurality of actuators 1015 and 1057. The suspension of the polarizer 1012, using the plurality of elastic elements 1019, serves to enhance oscillations experienced by the polarizer 1012.

Figure 11:
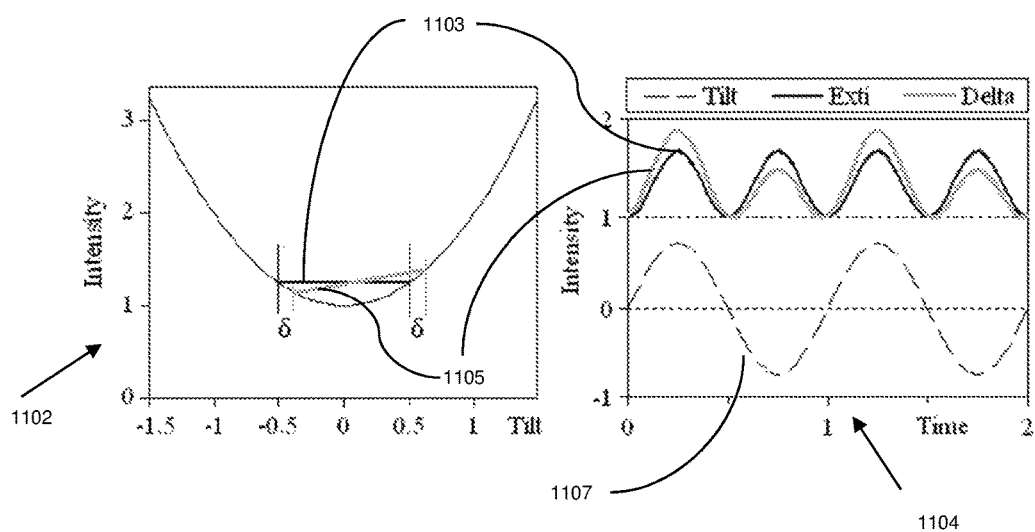
FIG. 11 shows a plot of the dependence of light intensity through the modulator against angle between polarization from using the third implementation of the drive mechanism shown in FIGS. 10E and 10F.

The results from using the third implementation of the drive mechanism are shown in FIG. 11. FIG. 11 shows a plot 1102 of the dependence of light intensity through the modulator against angle between polarization and polariser. The plot 1104 is the dependence of light intensity through the modulator against time (right). In each of the plots 1102 and 1104, the reference numeral 1103 denotes the results obtained when the rotation stage is set to extinction, while the reference numeral 1105 denotes the results obtained when the rotation stage set at an angle δ with respect to the extinction. The lock-in amplifier 1005 will give zero output for the case 1103; but for the case 1105, it will give positive output voltage proportional to the value of δ.

The actuator 1015 is preferably a piezo-electric strip, although a bimetallic strip may also be usable. The size of the polarizer 1012 is around 8 mm by 12 mm, the diameter of the actuator 1015 is around 13 mm. The protection box 1037 has length 1041 and breadth 1043 both of around 35 mm, and height 1045 of around 16 mm. The resonance frequency is around 242 Hz. At operating voltage 40 V peak to peak at resonance, the tilt of the polarizer 1012 is around 1 milliradian. With 3 mW laser at 650 nm, using a silicon photo-detector for the detector 1006 (refer FIG. 10A), a digital function generator 1007 and an analogue phase-lock amplifier 1005, measurement of polarisation rotation is achieved with sensitivity of 1 microradian.

To measure small values of rotation of light polarization, the best sensitivity is obtained usually polarization modulation techniques. The detection stage 508 shown in FIG. 10A is based on a polarization modulation technique that is sensitive enough to measure small values of rotation of light polarization. Further, as the detection stage 508 does not use any magnetically driven modulator, the detection stage 508 is not affected by magnetic field, thereby providing an advantage over systems which are affected by magnetic field. Such systems include a Faraday effect modulator which has light go through a paramagnetic medium in a coil where the oscillating current produces tilt of polarization; and an ellipsometer which uses a rotating polaroid and retarder driven by a motor which is affected by magnetic field. The drive mechanism of the detection stage 508 is in the millimeter range which allows use in optical systems, where space is limited. This provides an advantage over a photo-elastic modulator (PEM), such as Model FS50 from "Hinds International", which has a large dimension.

The manufacture cost of the optical head provided by the components shown in FIGS. 10E and 10F can be kept around $40, which allows it to be mass produced, as compared to the Model FS50 from "Hinds International", which costs around $4000. It is also possible to have the optical head used as a remote magnetic field sensor (RMFS) so that it can be attached instead of a Hall probe to an existing power supply. The same optical head can be used as a remote tensometer. In this case, the sample to be measured is a material with known opto-elastic constant placed, where the strain has to be measured. The strain induces birefringence and hence rotation of polarization. Once the rotation is calibrated versus strain for certain sample, the strain can be measured using this remote tensometer.

The detection stage 508 shown in FIG. 10A combines three features in one device. It is compact, cheap and not affected by magnetic field. It provides a polarization modulator that can be applied in systems, where magneto-optical Kerr effect is used to measure magnetic properties of materials or for remote detection of magnetic field.

Figure 12A:
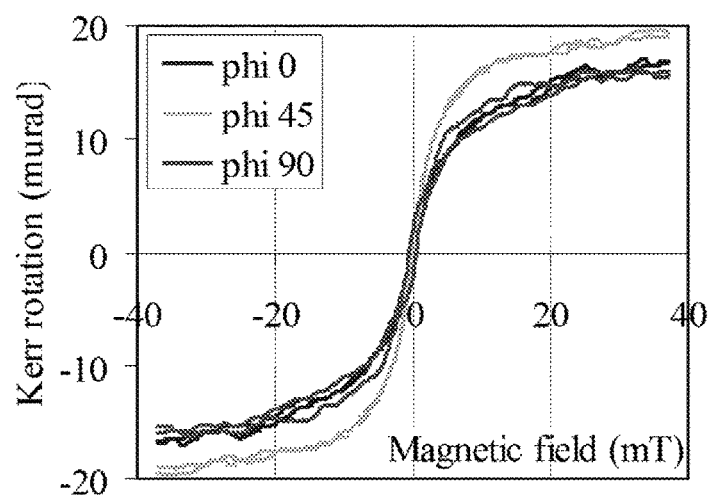
FIG. 12A shows results of using the detection stage of FIG. 10A to study magnetic materials having magneto-optical Kerr effect.

FIG. 12A shows results of using the detection stage 508 to study magnetic materials having magneto-optical Kerr effect. Typical value of polarisation rotation in one atomic layer of magnetic metal is 15 microrad, so that the detection stage 508 allows measurement of monolayer films.

Figure 12B:
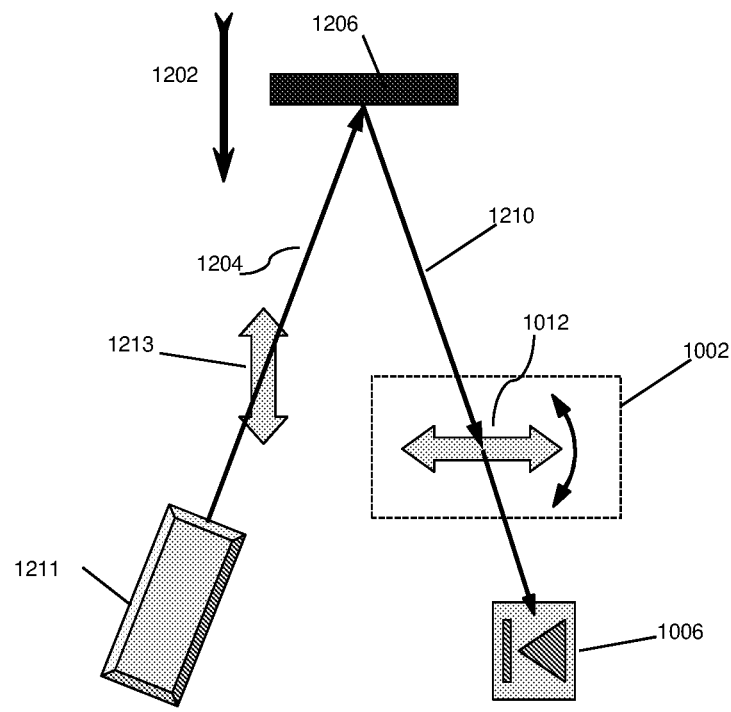
FIG. 12B shows a schematic where the detection stage of FIG. 10A is used for remote detection of magnetic field, where wired measurement is not available.

FIG. 12B shows a schematic where the detection stage 508 may be used for remote detection of magnetic field, where wired measurement is not available. This allows magnetic field measurement, where wires cannot reach, e.g. in harsh conditions 0 deg K to 600 deg C., or in a vacuum. Here a beam of polarized light 1204, from light generated by a laser source 1211 passing through a polarizer 1213 and goes to a sample 1206 exposed to a magnetic field 1202 (or there may be no magnetic field 1202 present, but the material is magnetic; or a magnetic field sensor; both not shown). The sample 1206 may be made in such a way that magneto-optical Kerr effect produces large rotation of polarization which is calibrated versus the magnetic field 1202. Reflected light 1210 goes through the polarization modulation stage 1002, having the polarizer 1012 to the detector 1006. The mean direction of the polarizer 1012 is set near extinction of the original polarization. The oscillations of the polarizer 1012 produce oscillations of the intensity going through; the amplitude and phase of these oscillations depend on the rotation of polarization of incoming light. Subsequent phase lock detection of the signal from the photo-detector 1006 (see FIG. 10A) allows measurement of the rotation of polarization. Another advantage is that the mean direction and modulation amplitude can be set independently.

Figure 13:
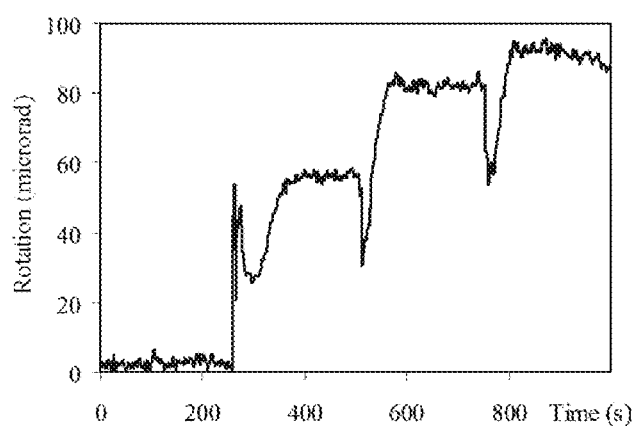
FIG. 13 shows the results of using the detection stage of FIG. 10A to measure rotation of polarisation of light passing through a 3 mm vessel with water and after adding sugar solution in various concentration steps.

FIG. 13 shows the results of using the detection stage 508 of FIG. 10A to measure rotation of polarisation of light passing through a 3 mm vessel with water and after adding sugar solution in steps of concentration 60, 100 and 120 mg/dl. The typical value of sugar concentration in human blood is around 70 mg/dl, which can be reliably measured. The transient peaks shown in FIG. 13 are due to finite time of mixing. The polarisation rotates by the angle proportional to the product of sugar concentration times length of light path in the solution.

Figure 14A:
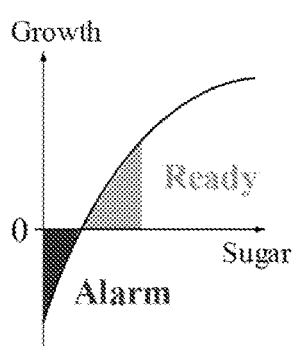
FIG. 14A shows the results of using the detection stage of FIG. 10A using the setup shown in FIGS. 14B and 14C.
Figure 14B:
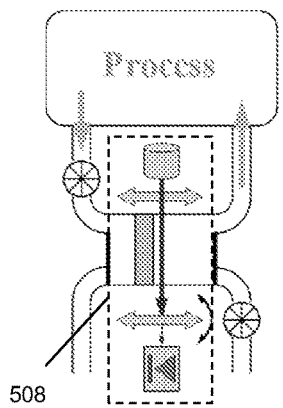
FIG. 14B shows instantaneous monitoring of sugar and flow during measurement.
Figure 14C:
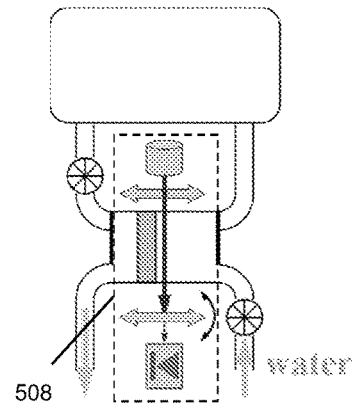
FIG. 14C shows flow at the time of rinsing and calibration

FIG. 14A shows the results of using the detection stage 508 of FIG. 10A using the setup shown in FIGS. 14B and 14C to monitor sugar concentration in a process, for example: yeast or yoghurt growth, or fermentation. It does not need consumable chemicals, only water to rinse the filter used in the setup. The duty cycle can be e.g. 55 sec measurement and 5 sec rinsing and calibration. FIG. 14B shows the instantaneous monitoring of sugar and flow during measurement. FIG. 14C shows the flow at the time of rinsing and calibration.

It will be appreciated by a person skilled in the art that numerous variations and/or modifications may be made to the present invention as shown in the embodiments without departing from a spirit or scope of the invention as broadly described. The embodiments are, therefore, to be considered in all respects to be illustrative and not restrictive.

The invention claimed is:

1. An ellipsometry system for measuring any one or more of molecular binding, adsorption and desorption on a substrate, the system comprising:
   (a) a cuvette comprising
      (i) a body within which a cavity is formed and an opening on the body, wherein the cavity extends into the opening through which the substrate is immersed;
      (ii) a window formed on each of two oppositely located walls of the body, wherein the windows are aligned to allow light to enter through one of the two windows to reflect off the portion of the substrate immersed in the cavity and exit through the other of the two windows;
      (iii) a channel arrangement enclosed within the body of the cuvette and comprising two non-contiguous portions, wherein one of the two non-contiguous portions guides fluid into the cavity and the other non-contiguous portion guides fluid out of the cavity;
   (b) a polarized light source disposed to provide the light that enters into one of the two windows on the body of the cuvette; and
   (c) a detection stage disposed to receive the light that exits through the other of the two windows on the body of the cuvette and including a polarizer and a detector disposed downstream of the polarizer to receive light transmitted through the polarizer, wherein the polarizer is suspended on a plurality of elastic elements spatially arranged to be each equally spaced apart, wherein the detection stage is configured to measure polarization rotation of the received light, the polarization rotation caused by any one or more of molecular binding, adsorption and desorption occurring on the substrate surface.

2. The ellipsometry system of claim 1, wherein the detection stage further comprises:
   a retarder disposed in the path of the received light for polarization state conversion of the received light; and
   a drive mechanism coupled to the polarizer to modulate the polarization of the light transmitted through the retarder, the drive mechanism configured to move the polarizer within a plane generally perpendicular to the direction of the received light.

3. The ellipsometry system of claim 2, wherein the drive mechanism comprises a platform coupled to the polarizer, wherein the platform is arranged to rotate around an axis that is generally parallel to the path of the received light, so that the rotating platform is configured to rotate the polarizer on the plane.

4. The ellipsometry system of claim 2, wherein the drive mechanism comprises an actuator coupled to the polarizer, wherein the actuator is configured to apply rotational motion to the polarizer along an arc that lies in the plane.

5. The ellipsometry system of claim 4, wherein the actuator comprises any one or more of a piezo-electric and a bimetallic strip.

6. The ellipsometry system of claim 4, wherein the actuator is coupled to the polarizer through an elastic element.

7. The ellipsometry system of claim 6, wherein the drive mechanism further comprises at least one further actuator, each coupled to one of the plurality of elastic elements, wherein the plurality of actuators are configured to oscillate the polarizer within the plane generally perpendicular to the direction of the received light.

8. The ellipsometry system of claim 7, wherein the drive mechanism further comprises: a sensor coupled to at least one of the plurality of elastic elements; and the detection stage further comprises a tuning circuit coupled to the sensor and the plurality of elastic elements, wherein the tuning circuit provides a driving signal to have the plurality of actuators operate at resonance frequency in response to a signal received from the sensor.

9. An ellipsometry system for measuring any one or more of molecular binding, adsorption and desorption on a substrate, the system comprising:
   a cuvette including a body with a cavity in which the substrate is immersed, a window formed on each of two oppositely located walls of the body, and a channel arrangement enclosed within the body and including two non-contiguous portions in which one of the two non-contiguous portions guides fluid into the cavity and one of the two non-contiguous portion guides fluid out of the cavity;
   a light source that provides light to the substrate located in the body of the cuvette;
   a polarizer that receives reflected light from the substrate; and
   a drive mechanism coupled to the polarizer and including an elastic member and an actuator, wherein the elastic member includes a plurality of elastic elements that are equally spaced apart to suspend the polarizer, and wherein the actuator moves the elastic member that moves the polarizer.

10. The ellipsometry system of claim 9, wherein the elastic member is a spring.

11. The ellipsometry system of claim 9, wherein the actuator moves the polarizer in a plane that is perpendicular to a direction of the reflected light from the substrate.

* * * * *